United States Patent [19]
Manspeizer

[11] Patent Number: 5,928,234
[45] Date of Patent: Jul. 27, 1999

[54] EXTERNAL FIXTURE FOR TRACKING MOTION OF A JOINT

[76] Inventor: Sheldon Manspeizer, 1 Autumn Ridge Rd., Pound Ridge, N.Y. 10576

[21] Appl. No.: 08/948,455

[22] Filed: Oct. 10, 1997

[51] Int. Cl.[6] .................................................. A61B 17/56
[52] U.S. Cl. .................... 606/61; 606/60; 606/62; 606/63; 606/54; 606/69; 606/70; 606/71; 606/86
[58] Field of Search .................. 606/61, 54, 86, 606/69, 70, 71

[56] References Cited

U.S. PATENT DOCUMENTS

| | | |
|---|---|---|
| 1,590,499 | 2/1926 | Cozad . |
| 1,789,060 | 1/1931 | Weisenbach ............................ 606/54 |
| 4,782,842 | 11/1988 | Fietti, Jr. . |
| 4,804,000 | 2/1989 | Lamb et al. . |
| 4,834,057 | 5/1989 | McLeod, Jr. . |
| 4,911,177 | 3/1990 | Lamb et al. . |
| 4,919,119 | 4/1990 | Jonsson et al. . |
| 5,102,411 | 4/1992 | Hotchkiss et al. . |
| 5,263,492 | 11/1993 | Voyce . |
| 5,514,143 | 5/1996 | Bonutti et al. ............................ 606/86 |

*Primary Examiner*—Michael Buiz
*Assistant Examiner*—Tan-Uyen T. Ho
*Attorney, Agent, or Firm*—Lerner, David, Littenberg, Krumholz & Mentlik, LLP

[57] ABSTRACT

A fixture is attached to the bones using external fixation techniques to trace a representation of the polycentric motion of a joint. The fixture has two plates attached to bones on respective sides of the joint. The plates are unconnected to each other and free to move relative to each other. The motion may be recorded using a stylus that traces a track in a deformable medium.

16 Claims, 2 Drawing Sheets

EXTERNAL FIXTURE FOR TRACKING MOTION OF A JOINT

FIELD OF THE INVENTION

The invention relates to the measurement of the path of movement of a joint, and specifically to an externally mounted fixture for the measurement of the polycentric motion of the knee or another joint.

BACKGROUND OF THE INVENTION

The motion of articulated joints in vertebrates, and specifically in humans, may involve extremely complex motion between the bones forming the joint. Certain joints, such as the human shoulder and hip, involve ball and socket joints producing a three dimensional angular motion. Other human joints, such as the knee and elbow, produce significantly more complex motions involving both angular and linear motion.

The human knee, for example, produces a "polycentric" motion wherein the center of rotation of the tibia with respect to the femur varies as a function of the angle of rotation. The polycentric motion is caused by the complex relationship of the various interacting surfaces involved in articulation of the knee. Those relationships include a sliding of the tibia relative to the femur, and a rotation of the tibia relative to the femur. The motion of the tibia relative to the femur is further complicated by the three-dimensional component of motion outside the sagittal plane, and by the contribution of ligaments, tendons and cartilage structure.

As a results of contributions from all these factors, a given point on the tibia typically traces a complex, non-linear curve in the three-dimensional coordinate system of the femur. That curve is difficult to predict from static measurements of the various anatomical features contributing to the curve shape, because of the large number of those features and the difficulty in accessing them. It is therefore desirable to have a method for directly measuring the relative motion of the bones on either side of a joint in order to describe the motion of that joint.

An accurate representation of the motion of a joint may be used in many applications. For example, braces for use in the healing of damaged or misformed joints should be designed to closely imitate the measured motion of a healthy joint. In U.S. Pat. No. 4,782,842 to Fietti, Jr., a device for setting a fractured wrist in disclosed wherein metacarpal bones in the hand are restricted to a defined motion relative the radius in the forearm. The movement is controlled by a pinion engaged with an arcuate rack, which defines a compound motion of the wrist. The wrist is moved through a predetermined arc of flexion or extension imitating the motion of the healthy joint. The path of a healthy wrist is approximated by a series of arcs in the rack having varying radii and centers of curvature.

The measurement of polycentric motion may also be used as a diagnostic tool to detect problems affecting the motion of a joint. If the motion of a healthy joint is known, either by averaging the joint motion of a number of other healthy individuals, or by measuring the joint motion of the individual in question at an earlier time, the current joint motion may be compared to the healthy joint motion to diagnose problems in joint mechanics. Appropriate corrective action may then be taken.

It may be advantageous to measure the joint motions of a large number of individuals, in order to determine average joint motions across various populations. Such measurements may be made using the joints of either cadavers or of healthy individuals. There is therefore a need for a simple, systematic, repeatable apparatus and method for measuring the path of motion of a large number of joints.

Devices exist for the measurement of the angle of motion of a joint. For example, in U.S. Pat. No. 5,263,492 to Voyce, a recording goniometer for measuring the angle of joint movement of a knee is disclosed. The device includes two extension members which are strapped to the upper and lower leg respectively. The extension members are pivotally connected by a pivot pin. One of the extension members supports a pencil, while the other extension member supports a paper disk. The angle of travel during extension and flexion of the knee is recorded by the pencil on the paper disk.

U.S. Pat. No. 1,590,499 to Cozad discloses a measuring instrument for measuring the angle of rotation of an elbow or other joint. The device includes trough-shaped members that are strapped to the limb above and below the joint. The trough-shaped members are connected by pivot hinges on both sides of the joint. A protractor is rigidly attached to one of the trough-shaped members, while an indicating arrow having a center at the center of the protractor is attached to the other of the trough-shaped members. Angulation of the joint is read by observing the location of the indicator on the scale of the protractor.

None of the above disclose a method and apparatus for tracing a representation of the path of motion of a joint. The present invention is directed to such a method and apparatus.

SUMMARY OF THE INVENTION

The present invention relates to a method and apparatus for measuring joint motion. In an apparatus according to the invention, a fixture is provided for attachment to first and second bones for recording motion of the joint therebetween. The fixture includes a first plate adapted for rigid attachment to the first bone, and a second plate adapted for rigid attachment to the second bone. Each of the first and second plates have joint ends for attachment near the joint. The first and second plates are unconnected and free to move with respect to each other.

The fixture further includes a recording instrument connected to the joint end of the first plate, and a recording medium connected to the joint end of the second plate. Upon rotation of the joint, the recording instrument interacts with the recording medium to record a representation of the motion of the joint. By rigidly connecting the plates only to the bones, and not to each other, the representation of motion is determined solely by the motion of the joint, and is not influenced by interconnections between the plates.

The recording instrument may be a stylus and the recording medium may be a deformable material. In that case, the second plate may define a cavity for receiving the deformable material, and the stylus may have a threaded shaft portion for mounting in a threaded hole in the first plate.

Each of the first and second plates may have orthopedic external fixation pins for rigid attachment of the plates to the respective bones. The first plate may be adapted for mounting the recording instrument to the joint end and may further be adapted to mount the recording instrument in any of a plurality of positions.

The first and second bones may be the tibia and femur, in which case the joint is the knee.

In a method for recording the motion of a joint according to the invention, a first plate is provided having a recording instrument attached to it. A second plate is provided having a recording medium attached to it. The second plate is unconnected to the first plate.

The first plate is rigidly attached to a first bone on one side of the joint, the second plate is rigidly attached to a second bone on the second side of the joint, and the recording instrument and the recording medium are engaged for recording relative motion of the plates. The joint is then flexed and the relative motion of the plates is traced by the recording instrument on the recording medium, recording a representation of the motion of the joint.

In one method according to the invention, the first plate is provided with a stylus, while the second plate is provided with a deformable material. In that case, the tracing step comprises forming a trace in the deformable material with the stylus.

The deformable material may be a solidifiable gel-like material, in which case the method further includes the step of solidifying the gel after tracing a representation of the relative motion. The stylus may have a threaded shaft portion engaged in a threaded hole in the first plate. In that case, the stylus may be turned in the threaded hole to adjust a depth of engagement of the stylus in the deformable material.

The steps of rigidly attaching the first and second plates to the bones may include inserting at least one orthopedic external fixation pin into the bone, and then securing the plate to the pin. The bones may be the tibia and femur, with the joint being the knee.

DETAILED DESCRIPTION OF THE PREFERRED EMBODIMENTS

Figure 1:
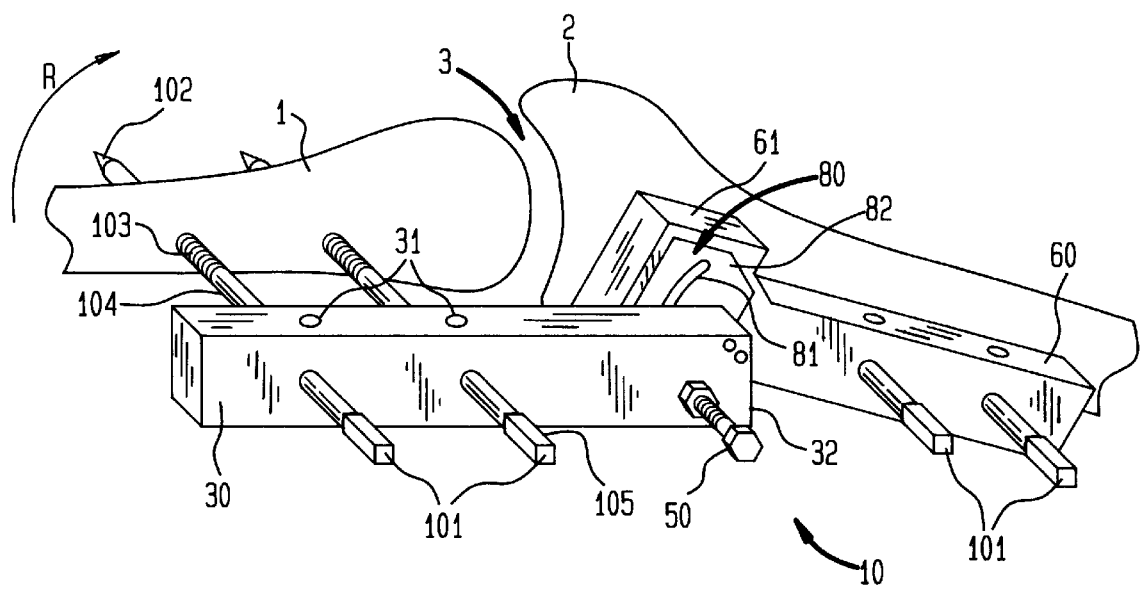
FIG. 1 is a perspective view of a fixture attached to a human femur and tibia, according to one embodiment of the invention.

A fixture 10 for tracking motion of a joint 3 (FIG. 1) includes a first plate 30 and a second plate 60. For purposes of clarity and conciseness, the fixture will be described as a fixture for measuring motion of a knee, although a similar fixture could be used to measure the motion of other joints, such as the wrist, the elbow and the ankle.

The first, or tibial, plate 30 is attached to the tibia 1 using orthopedic bone pins 101. Such bone pins are known in the art, and comprise a fluted, cutting tip 102, a threaded portion 103, suitable for anchoring in the cortical portion of the bone, a smooth portion 104 for passing through the skin and a driver portion 105 having wrench flats or other driving means.

The bone pins 101 are rigidly attached to the first plate 30 using set screws (not shown) installed in threaded cross holes 31. Alternatively, the bone pins may be attached to the plate 30 by others means such as collets, chucks or clamps. In any attachment means it is important that no relative motion is permitted between the bone pins 101 and the plate 30, so that the plate 30 precisely tracks the motion of the bone 1.

A second plate 60 is attached to the femur 2 using an additional set of bone pins 101. Like plate 30, the plate 60 is rigidly attached to the bone so that it precisely tracks the motion of the femur 2.

The first plate 30 and the second plate 60 are unconnected. The term "unconnected" as used herein means that there is no direct connection between the first and second plates that restricts the motion of one with respect to the other. Unconnected plates would include plates attached by a chain or a cable, which would permit the plates to move freely with respect to each other. On the other hand, plates are not unconnected if they are attached by a pivot or a linkage that restricts or defines their relative movement.

While two bone pins are shown retaining each of the plates 30, 60, additional bone pins may be used in order to more rigidly attach the plates. In a currently preferred embodiment, three bone pins are used for attaching each of the plates. In addition to increasing the number of bone pins retaining the plate, increasing the distance between the bone pins will more securely attach the plate to a respective bone, by increasing the resisting moment exerted by the bone pins against relative motion of the plate with respect to the bone.

Figure 2:
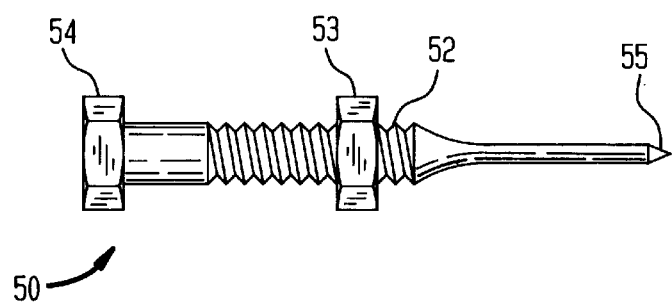
FIG. 2 is a plan view of a stylus of the fixture of FIG. 1.

A recording instrument 50, which in a preferred embodiment is a stylus, is attached to the first plate 30 at the end 32 nearest the joint 3. A tip 55 (FIG. 2) of the stylus 50 extends from the plate 30 in a direction toward the bones 1, 2 (FIG. 1).

The plate 30 is spaced apart from the bone 1 by the pins 105 a distance greater than the plate 60 is spaced apart from the bone 2. A joint end 61 of the plate 60 may thereby extend between the plate 30 and the bones 1,2. A recording medium, which in the preferred embodiment is a clay-like deformable material 80, is attached to the joint end 61 of the plate 60. The juxtaposition of the joint end 32 of the plate 30 and the joint end 61 of the plate 60 permits the stylus 50 to engage the deformable material 80.

A rotation of the tibia 1 in a direction of arrow R causes the stylus 50 to trace a track 81 in the deformable material 80. Because the plates 30, 60 are unconnected and free to move relative to each other, the relative motion of the plates, and therefore the shape of the track 81, is completely controlled by the motion of the joint 3.

In the case of the human knee, the rotation R of the tibia 1 with respect to the femur 2 has large components in the sagittal plane. The deformable material 80 is therefore placed so that an upper surface 82 of the material is substantially parallel with the sagittal plane. The trace 81, viewed as a two-dimensional figure on the plane of the upper surface 82 of the deformable material 80, is therefore a two-dimensional representation of the motion of the joint 3 in the sagittal plane.

The complex motion of a joint such as a knee, however, involves rotation and displacement in planes other than the sagittal plane. For that reason, in a preferred embodiment of the invention, the recording instrument 50 is capable of recording relative motion of the two plates in three dimensions. In the embodiment where the recording instrument 50 is a stylus and the recording media 80 is a deformable material, the depth of the track 81 formed by the stylus in the deformable material is indicative of joint movement outside the sagittal plane. Thus, the track 81 may represent the three dimensional motion of the joint 3. For example, in a test conducted by the inventor, a track 81 formed by a stylus in a deformable material, was 1½ inches long in the sagittal plane and varied in depth approximately 3–4 mm along its length.

In a preferred embodiment of the recording instrument according to the invention, the stylus 51 (FIG. 2) has a threaded portion 52 for attachment to the plate 30. A head 54 of the stylus 51 has wrench flats for adjusting the depth to which the stylus is set with respect to the plate 30. A lock nut 53 is provided for locking the stylus 51 in place on the plate 30.

The stylus further has a tip 55 for tracing a track in the deformable material 80. The tip 55 of the stylus 51 may have a conical end for forming a V-shaped groove in the deformable material 80, which may later be measured with a ball probe to create a precise three-dimensional description of the groove. The ball probe (not shown) is seated in the groove formed by a conical end 55 of the stylus to provide an indication of both the depth of the groove and of the shape of the curve in the sagittal plane, simultaneously. Such an arrangement may be employed, for example, using a coordinate measuring machine.

Alternatively, the stylus may have a spherical tip or a truncated cylindrical tip, or may have a tip of another shape. Ideally, the shape of the stylus tip will form a groove that is easily measured in three dimensions.

By providing a stylus having an adjustable depth with respect to the plate 30, the plates 30, 60 may be installed on the bone pins 101 without precise alignment for the purpose of forming a predetermined groove depth. Instead, the initial depth of the groove is set by adjusting the stylus after fixing the plates to the bones.

Figure 3:
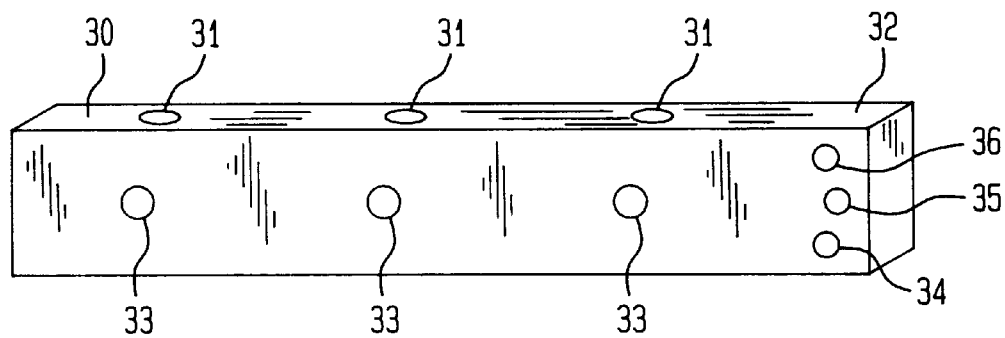
FIG. 3 is a perspective view of a tibial plate of the fixture of FIG. 1.

The first or tibial plate 30 (FIG. 3) has a plurality of holes 33 for receiving and rigidly attaching to the bone pins 101. The plate may be provided with set screw holes 31 intersecting the holes 33 in order to install set screws for locking to the bone pins 101 to the plate. Preferably, the holes 33 are spaced apart as far as is practical in order to provide maximum rigidity in the connection between the plate 30 and the bone.

At the joint end 32 of the plate 30, a plurality of holes 34, 35, 36 are provided for receiving the stylus 50 in a plurality of alternative locations. The stylus 50 may thereby be installed in the plate 30 so as to center the trace 81 in the deformable material 80.

In the preferred embodiment, the first plate 30 is approximately 8 inches in length. In the example shown, the plate is approximately 1 inch in thickness and approximately 1½ inches in width, and the bone screw holes 33 are spaced apart from each other approximately 2 inches. The plate may be formed from aluminum, stainless steel, titanium, plastic materials or any other material with sufficient strength and stiffness to permit rigid attachment to the bone and rigid support of the stylus.

Figure 4:
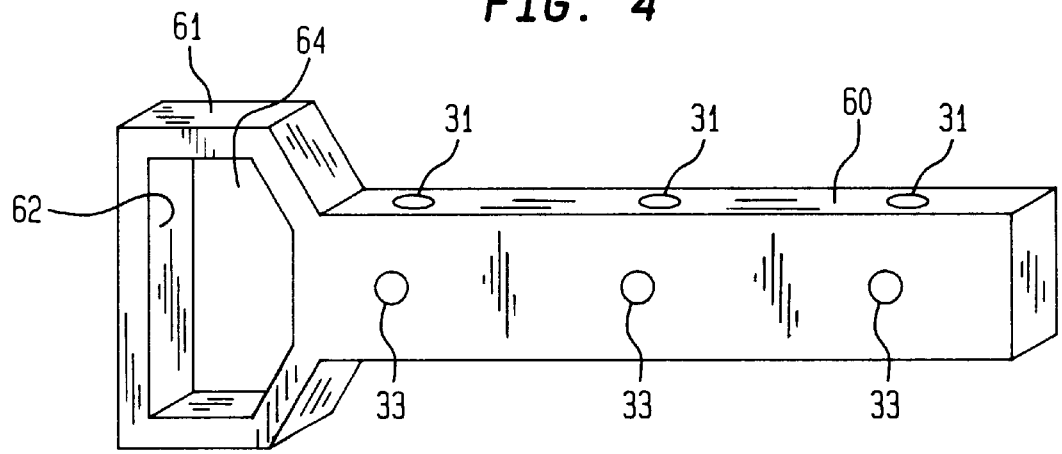
FIG. 4 is a perspective view of a femoral plate of the of FIG. 1.

The second plate 60 (FIG. 4) has bone screw holes 33 arranged in a manner similar to those of the first plate 30. The second plate 60 has an enlarged joint end 61 defining a cavity 62 for receiving the deformable material 80. The second plate 60 is also approximately 8 inches long, has a thickness of 1 inch, and, for most of its length has a width of about 1.5 inches. The enlarged joint end, however, has a width of about 3 inches. The cavity 62 is approximately 0.75 inches deep, and has a substantially flat cavity floor 64.

Figure 5:
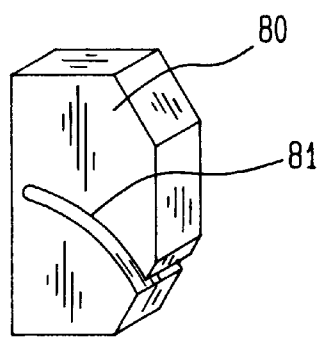
FIG. 5 is perspective view of a mass of deformable material having a trace representing the relative movement of two plates traced thereon, according to one embodiment of the invention.

In a preferred embodiment of the invention, the recording medium is a moldable material 80 (FIG. 5) which may be formed to fill the cavity 62 of the plate 60. The moldable material may be a gel-like material that may be solidified after the trace 81 is formed with the stylus 50. For example, the material may be a gel that is in a semi-solid state during tracing of the joint motion, but which can be hardened through the use of an additive to convert the material to a solid state after the track is formed on the material. Alternatively, the material may be a two-part epoxy, wherein the pattern is traced after mixing the epoxy, but before the epoxy hardens. In yet another embodiment, the deformable material may be a temperature-curing or air-curing substance that is fixed through the application of heat or simply by exposure to ambient air.

The trace 81 formed in the deformable material 80 is representative of the complex motion of the joint 3. Because the plates 30, 60 are unconnected and free to move relative to each other, the shape and depth of the trace 81 is entirely controlled by the motion of the joint. The detailed geometry of the trace 81 may be determined by measuring the trace using a coordinate measuring machine, optical measurement means or traditional bench measuring equipment such as a dial indicator. As noted above, information from the trace may be used for several purposes including the design of a brace for the support of a joint.

For certain applications, it is important to establish the spatial location of the trace with reference to the measured joint. Thus, in installing the plates 30, 60, a spatial relationship must be established between the joint 1, the recording medium 80 and the recording instrument 50. That spatial relationship may be established by aligning the plates with the bones using x-ray visualization of the underlying bones, or by using templates keyed to anatomical landmarks on the bones. The coordinate information regarding the location of the trace with respect to the joint may then be used in order to convert data from a series of measurements of the trace into information describing the joint, or information useful in the design of a brace, etc.

To use the fixture according a method of the invention, the first and second plates are first attached to the bones using the orthopedic pins. The plates themselves may be used as templates for installing the bone pins. The plates 30, 60 must be positioned in a predetermined location with respect to the joint 3, and relative to each other in order to provide a readable trace. In the case of a living patient, standard external fixation techniques known in the art are employed.

The deformable material 80 is placed in the pocket 62 of the plate 60 either before or after the plate 60 is installed on the bone. The stylus 50 is placed in one of the three stylus holes 34, 35, 36 of the plate 30 for optimum placement of the stylus within the deformable material 80.

After attachment of the plates, the joint 3 (FIG. 1) is rotated in the direction of arrow R. In the case of a knee joint, the tibia 1 is rotated in a posterior direction with respect to the femur. Upon rotation of the knee the stylus 50 traces a track 81 in the deformable material 80. That track is a representation of motion of the joint.

The procedure may be repeated on a plurality of cadavers or living patients in order to determine an average joint motion and a variability among populations. Such information is very useful in the design of braces or prosthetics that are manufactured in a standard size or sizes. Alternatively, the motion of the joint of an individual may be determined for custom design of a brace or prosthetic for that individual.

As will be readily appreciated, numerous variations and combinations of the features discussed above can be utilized. For example, in using the fixture of the invention with a knee, the roles of the tibial and femoral plates may be reversed; i.e., the tibial plate may carry the deformable material and the femoral plate may carry the stylus. Additionally, other techniques for recording the two- or three-dimensional motion of the joint may be used, such as optical measurement means, electromechanical means, pencil and paper or other motion-recording means. As these and numerous other variations and combinations of the features discussed above may be employed without departing from the present invention, the foregoing description of the preferred embodiment should be taken by way of illustration, rather than by way of limitation, of the invention as claimed.

We claim:

1. A fixture for attachment to first and second bones for recording motion of a joint therebetween, comprising:

(a) a first plate adapted for rigid attachment to the first bone;

(b) a second plate adapted for rigid attachment to the second bone, said first and second plates being unconnected;

(c) a recording instrument connected to said first plate; and (d) a recording medium connected to said second plate;

whereby, upon rotation of the joint, said recording instrument interacts with said recording medium to record a representation of motion of the joint.

2. A fixture as claimed in claim 1, wherein said recording instrument is a stylus and said recording medium is a deformable material.

3. A fixture as claimed in claim 2, wherein said second plate defines a cavity for receiving said deformable material.

4. A fixture as claimed in claim 2, wherein said stylus has a threaded shaft portion and said first plate defines at least one threaded hole for mounting said threaded portion of said stylus.

5. A fixture as claimed in claim 1, further comprising a plurality of orthopedic external fixation pins for said rigid attachment of said first and second plates to the first bone and second bone, respectively.

6. A fixture as claimed in claim 1, wherein said first and second plates have respective joint ends for attachment near the joint, and said recording instrument and recording medium are connected to joint ends of respective plates.

7. A fixture as claimed in claim 6, wherein said first plate is adapted for mounting said recording instrument to said joint end in a plurality of positions.

8. A fixture as claimed in claim 1, wherein one of the first and second bones is a tibia, the other of the first and second bones is a femur and the joint is a knee.

9. A fixture as claimed in claim 1, wherein the first bone is a tibia, the second bone is a femur and the joint is a knee.

10. A method for recording a representation of motion of a joint, comprising the steps of:

providing a first plate having a recording instrument attached thereto;

providing a second plate having a recording medium attached thereto, said second plate being unconnected to said first plate;

rigidly attaching said first plate to a first bone on a first side of the joint;

rigidly attaching said second plate to a second bone on a second side of the joint;

engaging said recording instrument and said recording medium for recording relative motion of said plates;

flexing the joint and tracing a representation of relative motion of said plates with said recording instrument on said recording medium, whereby a representation of the motion of the joint is recorded.

11. A method as claimed in claim 10, wherein said step of providing a first plate with a recording instrument comprises the step of providing a first plate with a stylus attached thereto, said step of providing a second plate with a recording medium comprises providing a second plate having a deformable material attached thereto, and said tracing step comprises forming a trace in said deformable material with said stylus.

12. A method as claimed in claim 11, wherein said deformable material is a solidifiable gel-like material, and said method further comprises solidifying said gel after said tracing step.

13. A method as claimed in claim 11, wherein said stylus has a threaded shaft portion engaged in a threaded hole in said first plate, and said method further comprises the step of turning said stylus in said threaded hole to adjust a depth of engagement of said stylus in said deformable material.

14. A method as claimed in claim 10, wherein at least one of said steps of rigidly attaching said first and second plates further comprises inserting at least one orthopedic external fixation pin in a respective one of the first and second bones, and securing a respective one of said plates to said at least one pin.

15. A method as claimed in claim 10, wherein one of the first and second bones is a tibia, the other of the first and second bones is a femur and the joint is a knee.

16. A method as claimed in claim 10, wherein the first bone is a tibia, the second bone is a femur and the joint is a knee.

* * * * *

UNITED STATES PATENT AND TRADEMARK OFFICE
CERTIFICATE OF CORRECTION

PATENT NO. : 5,928,234
DATED : July 27, 1999
INVENTOR(S) : Manspeizer

It is certified that error appears in the above-identified patent and that said Letters Patent is hereby corrected as shown below:

Column 1, line 32, "results" should read --result--.

Column 1, line 47, "in" should read --is--.

Column 3, line 40, after "the" insert --fixture--.

Column 6, line 37, after "according" insert --to--.

Signed and Sealed this

Twenty-eighth Day of December, 1999

Attest:

Q. TODD DICKINSON

*Attesting Officer*   *Acting Commissioner of Patents and Trademarks*